United States Patent
De Braak et al.

(10) Patent No.: US 9,354,160 B2
(45) Date of Patent: May 31, 2016

(54) DEVICE FOR TESTING AN OPTIC

(71) Applicant: Dovideq Medical B.V., Deventer (NL)

(72) Inventors: Menno S. De Braak, Almelo (NL); Albertus J. Dommerholt, Holten (NL)

(73) Assignee: DOVIDEQ MEDICAL B.V., Deventer (NL)

( * ) Notice: Subject to any disclaimer, the term of this patent is extended or adjusted under 35 U.S.C. 154(b) by 827 days.

(21) Appl. No.: 13/686,025

(22) Filed: Nov. 27, 2012

(65) Prior Publication Data

US 2013/0208106 A1    Aug. 15, 2013

(51) Int. Cl.
| | |
|---|---|
| *G01N 21/17* | (2006.01) |
| *G01M 11/00* | (2006.01) |
| *G01M 11/02* | (2006.01) |
| *G01M 11/08* | (2006.01) |

(52) U.S. Cl.
CPC .............. *G01N 21/17* (2013.01); *G01M 11/00* (2013.01); *G01M 11/0235* (2013.01); *G01M 11/0264* (2013.01); *G01M 11/088* (2013.01)

(58) Field of Classification Search
CPC ............ G01M 11/00; G01M 11/0235; G01M 11/088; G01M 11/0264; G01N 21/17
See application file for complete search history.

(56) References Cited

U.S. PATENT DOCUMENTS

| | | | |
|---|---|---|---|
| 4,613,232 A | 9/1986 | Diener | |
| 5,699,440 A * | 12/1997 | Carmeli | H04N 17/002 348/180 |
| 5,820,547 A | 10/1998 | Strobl | |
| 6,498,642 B1 | 12/2002 | Duckett | |
| 6,734,958 B1 * | 5/2004 | MacKinnon | G01M 11/00 250/228 |
| 8,382,657 B1 * | 2/2013 | Bodor | A61B 1/00057 600/101 |
| 2003/0100818 A1 * | 5/2003 | Lei | G01M 11/00 600/117 |
| 2003/0107726 A1 * | 6/2003 | Hirt | G01M 11/33 356/73.1 |
| 2005/0049457 A1 * | 3/2005 | Leiner | G01M 11/00 600/117 |

FOREIGN PATENT DOCUMENTS

| | | |
|---|---|---|
| EP | 1187496 B1 | 5/2002 |
| GB | 2215077 A1 | 9/1989 |
| WO | 9841826 A1 | 9/1998 |

* cited by examiner

*Primary Examiner* — Jeffrey Harold
*Assistant Examiner* — Sean Haiem
(74) *Attorney, Agent, or Firm* — Oppedahl Patent Law Firm LLC (57) ABSTRACT

A device for testing an optic which is mountable thereon and has a central axis extending in the longitudinal direction thereof, comprising a test image, a test image table for supporting the test image, a light source for lighting the test image via the optic mountable thereon, an attaching device for mounting the optic mountable thereon, detection means placed on the attaching means for detecting the lighted test image, first guide means and second guide means co-acting with the first guide means and extending in longitudinal direction thereof for the purpose of positioning the test image table along a substantially straight line relative to the attaching device, and a signal processing device for receiving, storing and comparing detection values of the lighted test image detected by the detection means to threshold values therefor specific to the optic and prestored in a database, whereby the optic can be tested quickly and without personal influences, with a reliable test result.

19 Claims, 7 Drawing Sheets

DEVICE FOR TESTING AN OPTIC

TECHNICAL FIELD

The invention relates to a device and a method for testing an optic which is mountable thereon and has a central axis extending in the longitudinal direction thereof, comprising a test image, a test image table for supporting the test image, a light source for lighting the test image via the optic which is mountable thereon, an attaching device for mounting the optic mountable thereon, detection means placed on the attaching means for detecting the lighted test image, first guide means and second guide means co-acting with the first guide means and extending in longitudinal direction thereof for the purpose of positioning the test image table along a substantially straight line relative to the attaching device, and a signal processing device for receiving, storing and comparing detection values of the lighted test image detected by the detection means to threshold values therefor specific to the optic and prestored in a database.

BACKGROUND OF THE INVENTION

A device according to the preamble and a related method are known from the international patent application 98/41836, which describes a device for testing an optic, such as testing for light loss during lighting of the optic, testing for reflection symmetry and testing for geometric distortions. In order to test these characteristics the device is provided with a test image to be positioned on a base along a straight guide and an attaching device to be positioned on the base via a rotation for the purpose of mounting the optic. After placing of the optic in the attaching device of the device according to international patent application 98/41836, the optic has two degrees of freedom for adjustment thereof relative to the test image. In order to block the degrees of freedom the test image and the attaching device can be respectively coupled non-translatably and non-rotatably to the base.

The known device comprises a camera which is provided with a lens for detecting the lighted test image which can be recorded by a computer system which has a memory provided with a database with threshold values. Each threshold value corresponds to a characteristic quantity for a determined test and is used to determine whether test results indicate acceptable or unacceptable performance characteristics. The test signals are compared for this purpose to the threshold values, which also depend on the type of test and the type of optic. The computer system thus analyses the test results and evaluates the performance of the optic and stores the test results and evaluations in a database, for instance for future consultation thereof.

The known device and the method for testing the optic according to this patent application has the drawback that placing of the optic in the device and setting thereof relative to the test image requires professional skill, requires knowledge of the specific optic to be tested, and is thus labour-intensive, which may result in inaccuracies and/or errors in the test results, whereby the reliability of measurements decreases and may result in an incorrect evaluation of the optic.

SUMMARY OF THE INVENTION

It is an object of the invention to provide a device and method for testing the optic quickly and without personal influences, with a reliable test result.

According to a first aspect, the object is achieved with a device according to the introductory paragraph, which is characterized in that the first and/or the second guide means are situated parallel to and at a distance from the central axis of the optic mountable thereon, and that the attaching device of the optic mountable thereon is adjustable relative to the test image along the longitudinal direction of the optic mountable thereon. Very reliable test results can be obtained with the device for testing the optic in this most advantageous embodiment, wherein a measurement error is minimized because only one degree of freedom need be adjusted during positioning of the optic mounted on the attaching device relative to the test image, wherein the degree of freedom coincides with the longitudinal direction of the optic mounted on the attaching device. The central axis of the optic to be mounted thereon coincides with the longitudinal axis of the device during use.

In an embodiment the first guide means are arranged on the attaching device and the second guide means are arranged on the test image table for relative displacement of the attaching device relative to the test image. A very precise and accurately determined displacement hereby becomes possible of the attaching device relative to the test image in the longitudinal direction of the optic mounted on the attaching device, without the attaching device having to be adjusted in translating manner relative to the test image transversely of the longitudinal direction of the optic mountable thereon and without the attaching device having to be adjusted in rotating manner relative to the test image.

In a further practical embodiment a servomotor is adapted to displace the attaching device relative to the test image in the longitudinal direction of the optic. It hereby becomes possible to position the attaching device at a desired distance relative to the test image without the intervention of a labour-intensive operation.

An above described device is known from US 2003/107726.

The device described in this patent application has the drawback that the device cannot test a placed medical optic fully automatically.

The device according to the invention has for its object to provide a test device which is able to fully test a placed medical optic.

The optic is provided for this purpose with identification elements and the device is provided with read elements for reading the identification elements. It hereby becomes possible to link the read elements to the signal processing device for the purpose of recognizing each optic mounted on the attaching device, wherein the signal processing device can retrieve data of the optic from a database in order to determine for instance the position of the attaching device relative to the test image.

In a further perfected, automated embodiment the identification elements comprise a barcode etched into the optic and the read elements comprise a barcode scanner. It hereby becomes possible to recognise the optic, wherein the barcode arranged on the identification elements can remain substantially unaffected under the influence of a cleaning treatment of the optic, wherein high temperatures and/or aggressive media may be used.

In a further automated, more specific embodiment the servomotor is adapted to drive a displacement of the attaching device relative to the test image subject to identification elements detected by the read elements. A highly automated test device hereby becomes possible, wherein the signal processing device can recognise the optic mounted on the attaching device using the read element and the identification element, can retrieve a value associated with this optic from a database, this value corresponding with the position of the attaching device relative to the test image, on the basis of which value the servomotor can be controlled for the purpose displacing the attaching device relative to the test image.

In a particularly practical, more universally specific embodiment the test image is mounted on a concavely formed surface of a spherical surface. It hereby becomes possible to test each optic mounted on the attaching device, irrespective of a visual angle of the optic. The visual angle of the optic is understood to mean the angle at which an outer end of the optic directed toward an object to be viewed is directed for the purpose of detecting the object. By positioning the outer end of the optic directed toward an object to be viewed at least close to and/or in the centre of the spherical surface a reference image corresponding to each optic can be detected.

In a generally essential embodiment the test image is provided with a pattern which comprises information distributed concentrically over the concavely formed surface relative to the centre of the spherical surface. In a particular embodiment the test image comprises a grid and/or a pattern of markers.

In a further automated and universal embodiment the detection means comprise a camera for detecting the test image, and the signal processing device is adapted to store received test image detections and compare them to threshold values therefor specific to the optic and prestored in a database. It hereby becomes possible to detect the test image via the optic, to make a recording of the test image which can be compared to a reference image stored in a database for an evaluation of the optic in respect of a shift of the grid and/or the pattern of markers, which shift can be a result of an incorrect alignment of the optic occurring during use.

In a preferred embodiment the device according to the invention comprises a test image housing with a substantially closed inner space provided with an at least partly spherical surface, the test image is arranged on the spherical surface and the test image housing comprises a throughfeed for throughfeed of a distal outer end of the optic. This test image housing ensures that the test results of the optic from the test device are not subject to ambient influences such as ambient light.

The throughfeed is preferably provided with centering means for centering the distal outer end of the optic in the throughfeed, and the centering means are preferably adapted to centre distal outer ends of different diameter. By centering the distal outer end of the optic the measurement is reproducible and the successive measurements on the same optic can be better compared with each other. The utility of the device is increased by making the centering means suitable for distal outer ends of different diameter.

In a preferred embodiment of the centering means, the centering means comprise two substantially V-shaped, co-acting centering parts at a certain mutual distance on the longitudinal axis of the throughfeed which, as seen in the line of the throughfeed, form a substantially lozenge-shaped passage, and the centering parts are movable adjustably between a first and second end position, wherein in the first end position the centering parts lie substantially at a right angle to the longitudinal axis of the throughfeed and in the second end position the centering parts each lie at an acute or obtuse angle relative to the longitudinal axis of the throughfeed such that the size of the lozenge-shaped passage is adjustable. With these centering means the distal outer end of the optic is supported at two separate positions along the central axis by the centering parts after placing in the centering means. The distal outer end is here also forced to run along the central axis.

In order to facilitate feed of the distal outer end into the test image housing, the test image housing preferably comprises a funnel-shaped part adjacently of the throughfeed for guiding the distal outer end of the optic to the throughfeed.

In a further preferred embodiment the test image housing is provided with a second light source. In this way it is possible to test only the image-guiding channels of the medical optic without making use of the light supply channels of the medical optic. No colour temperature change hereby occurs during lighting of the test image as a result of these light supply channels.

The second light source preferably comprises a plurality of light elements such as LEDs distributed over the inner housing, and the device also comprises means for controlling the individual light elements. The light elements are preferably distributed over a plane through which the longitudinal axis of the throughfeed also runs. When a light intensity measurement is performed, all light elements are preferably switched on. For the purpose of lighting the test image it is sufficient to switch on the light elements placed opposite the test image.

The colour temperature change occurring in the light supply channels can also be measured by placing an additional camera at the connection for the first light source. In addition, it is possible to count the number of defective light supply channels, which often consist of fibres, by means of a camera recording.

A further drawback of the prior art is that an inaccurate colour measurement can be performed with the device applied in the international patent application 98/41836, whereby the reliability of measurements and an associated evaluation of the optic may result in a further incorrect evaluation. In a specific automated embodiment according to the invention the detection means comprise a colour analyser for determining a colour of the light which the test image projects onto the colour analyser, and the signal processing device is adapted to store and compare received colour detections to the threshold values therefor specific to the optic and prestored in a database. It hereby becomes possible to measure the colour of the light which the test image projected onto the colour analyser. In order to determine the colour, the colour analyser comprises a first filter for filtering substantially light with a red colour, a second filter for filtering substantially light with a green colour and a third filter for filtering substantially light with a blue colour. Such colour analysers are per se known in the field of television stations where the quality of recording and reproduction is very important. Such colour analysers are very accurate, and such an accuracy has as yet not been found to be a necessary measure in testing optics in this field. An examination by eye followed by a personal evaluation thereof has sufficed in the field of testing optics. Cameras are used in this field, particularly CCD cameras, but these are not able to accurately determine the colour of the light projected by the test image onto the colour analyser.

Yet another drawback of the prior art is that with the device applied in the international patent application 98/41836, after use of the optic, moisture may be present in the optic during cleaning and cannot be measured directly with the device according to the international patent application 98/41836. In a specific embodiment the detection means comprise a moisture measuring device for detecting moisture, at least close to lens transitions in the optic, and the signal processing device is adapted to store and compare received moisture detections to the threshold values therefor specific to the optic and prestored in a database. It hereby becomes possible to test an optic mounted on the attaching device for the presence of a quantity of moisture and to evaluate the optic as to whether the quantity of moisture present in the optic exceeds a predetermined threshold value for the purpose of approving or rejecting the optic.

In a particular, specific embodiment the moisture measuring means comprises a microwave sensor for generating a microwave directed through the optic and for receiving a signal influenced by a lens transition and directed toward the microwave sensor. It hereby becomes possible to transmit microwaves through and receive them back from the optic, wherein the condition of received microwaves is a measure of the quantity of moisture present in the optic. The received microwaves can be detected by the sensor and communicated to the signal processing device for storing, processing and comparing to the predetermined threshold value for the purpose of evaluating the optic.

In an extended and further optimized embodiment the camera is provided with adjusting means for focussing a lens of the camera on the different lens transitions of the optic, wherein the adjusting means can be controlled by the signal processing device to focus on the lens transitions of the optic subject to setting values specific to the optic and stored in the database. It hereby becomes possible to test the optic fully automatically for the presence of moisture at one or more critical location specific to each optic. The adjusting means of the camera can be controlled by the signal processing means subject to the values stored in the database for each optic mountable on the attaching device.

The detection means preferably comprise a light intensity meter for determining the intensity of the light exiting the optic close to the proximal outer end, and the signal processing device is adapted to store and compare the measured light intensity to threshold values therefor specific to the optic and are pre-stored in a database. It hereby becomes possible to test the optic fully automatically for loss of light intensity in each optic. The adjusting means of the camera can be controlled by the signal processing device subject to values stored in the database for each optic mountable on the attaching device.

In an ideal embodiment the attaching device is adapted to receive different types of optic which each have a different eyepiece.

The attaching device preferably comprises for this purpose two co-acting housing parts, wherein:
- the first housing part has a passage for throughfeed of at least a part of the tapering part of the eyepiece, or an extension thereof,
- the first housing part has a tapering collar intended for the purpose of receiving the tapering part of the eyepiece,
- the second housing part is intended for the purpose of receiving the free outer end of the eyepiece,
- the second housing part is intended to be clampingly received in the first housing part.

These measures ensure that the eyepiece can be attached to the device in inventive but very effective manner.

In a specific and further extended embodiment the test image comprises a narrow continuous opening at the position of an extended central axis in the longitudinal direction of the optic mountable in the attaching device, and a micro-camera is placed close to the test image on a side thereof remote from the optic mountable in the attaching device. It hereby becomes possible to direct a micro-lens of the micro-camera at the continuous opening in order to make a recording of the tip of the optic, particularly the tip of the illuminated optic, so that the optic can be checked for breaks in glass fibres present in the optic.

According to a second aspect, the invention provides a test image for measuring shifts in the image of optics, wherein the test image is mounted on a concavely formed surface of a spherical surface. The test image makes a universal reference image possible which can be detected with any optic, irrespective of the visual angle of the optic, for the purpose of testing the optic, for instance for the degree of alignment. The visual angle is the angle at which an outer end of the optic facing toward an object to be viewed is directed in order to detect the object. In the practice of users of such optics use is made of a range of different types of optic, wherein users have a choice of optic with different visual angles. By positioning the outer end of the optic facing toward an object to be viewed at least close to and/or in the centre of the spherical surface a corresponding reference image can be detected with each optic.

BRIEF DESCRIPTION OF THE DRAWINGS

The invention will now be further elucidated on the basis of a preferred embodiment with reference to the accompanying figures, in which.

BEST MODE FOR CARRYING OUT THE INVENTION

The present invention is highly suitable for testing medical optics. In practice surgeons make use of optics on a large scale, such as an endoscope, a laparoscope, an arthroscope, a bronchoscope or urology optics, which provide a view of parts in the human and/or animal body to be examined and/or treated. Cleaning of the optic takes place after use thereof in order to make the optic suitable for use in a subsequent treatment of a subsequent patient. During cleaning of the optic in an autoclave the optic is exposed to both cleaning agents and high temperatures, which can have a degenerative effect on the optic. Before further use of the optic, for reasons of patient safety the optic must first be tested as to whether further use is safe or whether the optic must be reconditioned or whether the optic may no longer be used. In practice the optic is often tested by eye for the sake of speed, wherein colour change of the optic is for instance employed as criterion. It will be evident that viewing colour change with the naked eye is inaccurate and that such a test is affected by personal influences of the person looking through the optic and by external conditions, such as the influence of ambient light.

Figure 1:
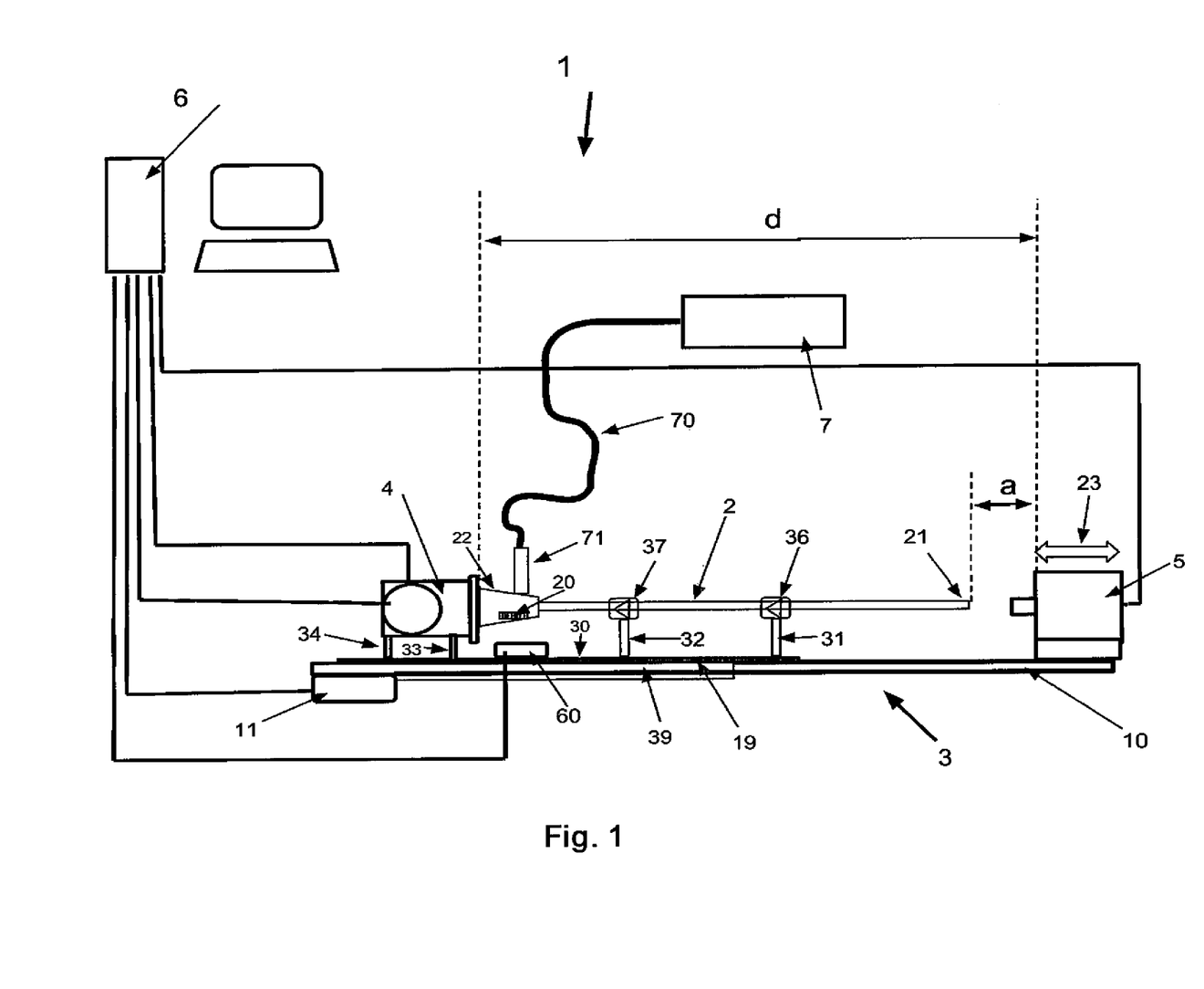
FIG. 1 shows a schematic side view of a device for testing optics according to the invention.

The device 1 shown in FIG. 1 provides an arrangement for systematic and accurate testing of optic 2 placed in device 1 without being affected by personal influences and external conditions. FIG. 1 shows optic 2 which is arranged in an attaching device 3 and which in this embodiment comprises a frame 30 on which a first support 31, a second support 32 are placed for supporting optic 2. For the purpose of clamping the optic 2, first and second supports 31, 32 are provided close to an outer end thereof remote from frame 30 with respectively a first and second holder 36, 37.

In this embodiment a third support 33 and a fourth support 34 are placed on frame 30 for supporting a first element 4. First element 4 comprises detection means for detecting a test image 50 which is visible through optic 2 and shown in FIGS. 3 and 4, and which is situated in a second element 5 at a variable distance d from first element 4. It is usual to illuminate test image 50 via a light inlet 71 which is present on optic 2 and which is in this embodiment coupled via a lead 70 to a light source 7. Optic 2 and inlet 71 thereof are provided with a plurality of glass fibres for guiding light coming from the light source. In an embodiment the optic 2 can comprise between 10 and 100 glass fibres extending parallel to each other in the longitudinal direction of optic 2 and situated in a sleeve, such as a cable or a cord.

In this embodiment second element 5 is disposed fixedly relative to a test image table or foundation 10 and frame 30 is disposed displaceably relative to foundation 10 in a direction as according to arrow 23, this direction substantially coinciding with the longitudinal direction of the optic 2 mountable on frame 30. Using the frame 30 displaceable relative to second element 5 as according to arrow 23, each optic 2 can be mounted in the device irrespective of the length of the optic 2. For displacement of frame 30 relative to foundation 10, in this embodiment foundation 10 is provided with guides or second guide means 19, and frame 30 is provided on a side thereof facing toward foundation 10 with first guide elements or guide means 39 co-acting with the guides or second guide means 19.

A skilled person will appreciate that positioning of optic 2 relative to second element 5 is achieved in alternative manner by disposing second element 5 for displacement in a direction as according to arrow 23 relative to a foundation 10, this direction substantially coinciding with the longitudinal direction of the optic 2 which can be mounted on frame 30, and disposing frame 30 fixedly relative to foundation 10. Using the second element 5 displaceable relative to frame 30 as according to arrow 23, each optic 2 can be mounted in the device irrespective of the length of the optic 2. For displacement of second element 5 relative to foundation 10, foundation 10 is for instance provided with guides (not shown) and second element 5 is for instance provided close to a side thereof facing toward foundation 10 with guide elements (not shown) co-acting with the guides. Arranging frame 30 fixedly relative to foundation 10 has the advantage that cabling, such as cords, coupled to the detection means is situated at a fixed position relative to the equipment to which the detection means are connected.

Attaching device 3 can be positioned manually relative to foundation 10. Device 1 is provided in this embodiment with a drive, such as a servomotor 11, for driving frame 30 relative to foundation 10. In order to control drive 11 device 1 is provided with a signal processing device 6 such as a computer 6 which, depending on the optic 2 present in attaching device 3, positions a first outer end 21 of optic 2 directed toward test image 50 at a predetermined value therefor at a desired distance a from test image 50. The data of optic 2 can be entered via computer 6 by the person carrying out the test. In this embodiment device 1 is provided with a read element, such as a barcode scanner 60, for reading an identification element, such as a barcode 20, which is arranged on a second outer end 22 of optic 2 facing toward first element 4. Read element 60 is coupled to computer 6 to process the read barcode 20, on the basis of which computer 6 determines a value from a database stored therein for the distance a at which computer 6 controls servomotor 11 for the purpose of driving frame 30 such that the first outer end 21 of optic 2 placed in attaching device 3 is situated at the desired distance a from test image 50. The skilled person will appreciate that in an alternative embodiment the drive, such as servomotor 11, can be adapted to drive second element 5 relative to foundation 10.

Figure 2:
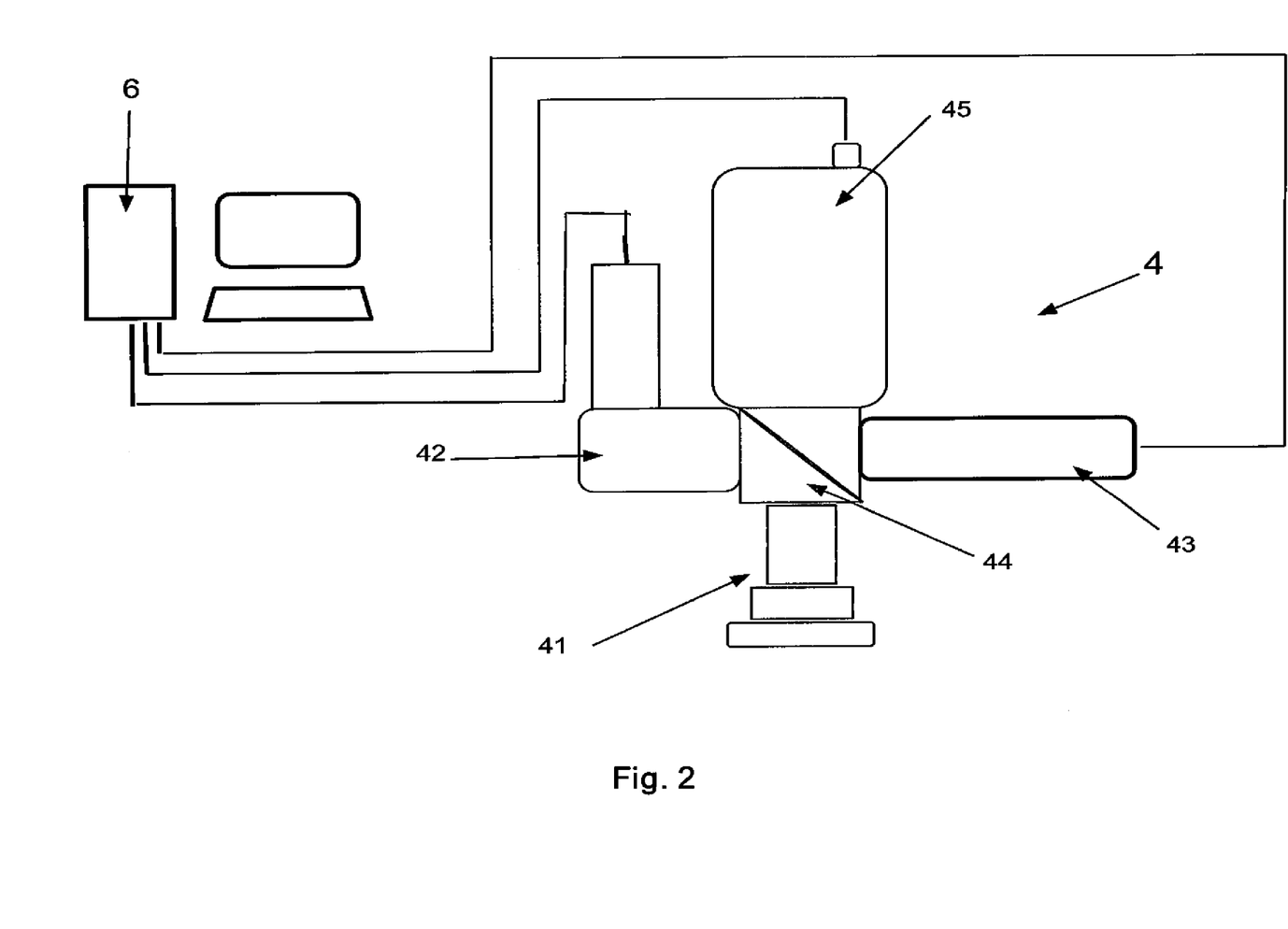
FIG. 2 shows a schematic top view of a first element in which detection means are disposed.

FIG. 2 shows first element 4 which comprises a focussing element 41, a colour analyser 42, a moisture meter 43, a beam splitter 44 and a camera 45, in particular an HD camera. Focussing element 41 is coupled in this embodiment to second outer end 22 of optic 2 and to beam splitter 44. The image of test image 50 visible via optic 2 is incident upon beam splitter 44, such as a 50% light-transmitting mirror, via focussing element 41, such as a lens, in order to project the optical image to colour analyser 42 and moisture meter 43. Using the detection means, such as colour analyser 42, moisture meter 43 and camera 45, optic 2 can be tested for respectively colour change of the lenses, for the presence of moisture in the lenses of optic 2 and for the presence of a curvature in optic 2.

With camera 45 a recording can be made of the test image 50 illuminated by the light source. Focussing element 41 is adapted to focus on the lens transitions present in optic 2, a recording of which can be made with camera 45. Focussing element 41 can be adjusted manually, wherein a person carrying out the test successively focuses focussing element 41 on the transitions of successive lens parts. According to the device of the invention focussing element 41 is provided with adjusting means for successively focussing thereof at a desired distance in optic 2. The data of optic 2 can for instance be entered via computer 6 by the person carrying out the test. According to a preferred embodiment the barcode scanner 60 is adapted to read barcode 20 arranged on a second outer end 22 of optic 2 facing toward first element 4. Read element 60 is coupled to computer 6 for processing the read barcode 20, on the basis of which computer 6 successively determines values from a database stored therein for successively focussing the focussing element 41 on the successive transitions of the lens parts.

Colour analyser 42 is adapted to receive light projected by test image 50 via focussing element 41. Colour analyser 42 is a per se known device which comprises a first, second and third filter for filtering respectively a red, green and blue colour of the light coming from test image 50, and comprises a first, second and third sensor diode. After the filters have acted the light not filtered out reaches a receiving element which corresponds with the filter and which determines the colour of this light in a range between a minimum value, which corresponds to completely white, and a maximum value which corresponds to completely black. In the absence of a change in colour of the lens parts present in the optic each receiving element detects a minimum value, such as zero or a value close to zero, of the light received by the receiving element.

Colour analyser 42 is coupled to computer 6 to process the signals detected by the receiving elements and corresponding to a measured colour of the filtered light. If the lenses of optic 2 have been adversely affected and cause a colour change in the light projected by test image 50, the receiving elements detect values which substantially vary from zero. Computer 6, which comprises a memory in which a database comprising threshold values for colour change is stored, compares the values to the threshold values. If the values of the colour have exceeded the threshold value, computer 6 generates a negative evaluation of optic 2. If the values of the colour have not exceeded the threshold value, computer 6 generates a positive evaluation of optic 2. If the values of the colour are within a range which includes the threshold value, computer 6 can generate an evaluation of optic 2 which lies between the negative and the positive evaluation, wherein advice is for instance given to use optic 2 one last time.

Moisture meter 43 is equipped in this embodiment with a sensor for transmitting and receiving modular microwaves which move through optic 2 in order to detect moisture in optic 2. Optic 2 is formed by a series of successive lens parts extending in the longitudinal direction of optic 2, wherein after cleaning of optic 2 moisture can accumulate at least close to transitions of successive lens parts.

In order to evaluate the quantity of moisture present, for instance close to a transition of the lens parts, the quantity of moisture received by the sensor is detected and stored in a database in the memory of computer 6. If the quantity of detected moisture has exceeded a threshold value, computer 6 generates a negative evaluation of optic 2. If the quantity of detected moisture has not exceeded the threshold value, computer 6 generates a positive evaluation of optic 2. If the differing composition is within a range including the threshold value, computer 6 can generate an evaluation of optic 2 which lies between the negative and the positive evaluation, wherein advice is for instance given to use optic 2 one last time.

Figure 3:
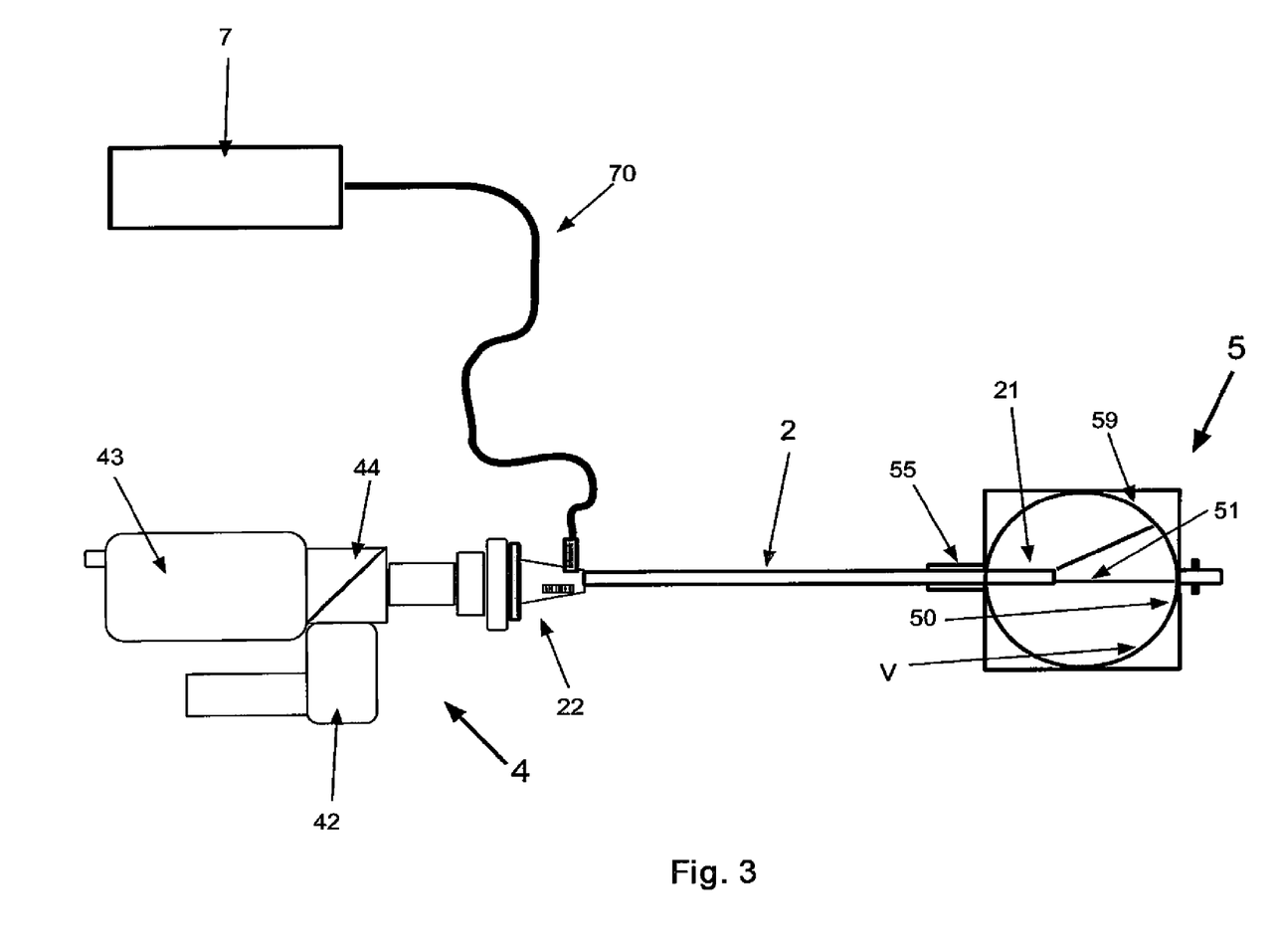
FIG. 3 shows a schematic top view of an optic which is coupled close to a first outer end to the first element and protrudes close to a second outer end remote from the first outer end into a second element which comprises a test image.

FIG. 3 shows the optic 2 which is coupled with the second outer end 22 thereof to the first element 4 described in FIG. 2 and which is inserted with first outer end 21 thereof into second element 5. Second element 5 comprises an opening 55 for throughfeed of a part of optic 2 situated close to first outer end 21. In the test position the first outer end 21 of optic 2 is situated in a centre 51 of second element 5. A part of second element 5 facing toward centre 51 has a concave form and forms an inner surface V of a spherical surface 59. Arranged on the inner surface V of spherical surface 59 is test image 50 which is provided with a grid which is formed by a series of first lines placed substantially parallel relative to each other and at a mutual distance, and a series of second lines which are placed substantially parallel to each other and at a mutual distance and which are directed substantially transversely of the first lines. In an alternative embodiment the test image 50, which is provided with reference points such as markers or a pattern of markers, is arranged on the inner surface V of spherical surface 59. In another alternative embodiment the test image 50, which is provided with a combination of the grid and the markers, is arranged on the inner surface V of spherical surface 59. Each point of inner surface V of the spherical surface is situated at substantially the same distance from the centre 51 of second element 5. Test image 50 provided with the grid and/or the markers is suitable for all optics 2, irrespective of a visual angle A as shown in FIG. 4 at which the outermost lens part situated close to first outer end 21 is placed.

The recording made with camera 45 can be stored in the database of computer 6 for comparing thereof to a reference image which is associated with optic 2 and stored in the database of computer 6 and which comprises a reference grid and/or reference markers. If the recording of the reference grid and/or reference markers includes a variation which exceeds a threshold value stored in the database, computer 6 generates a negative evaluation of optic 2. If the recording of the reference grid and/or reference markers includes a variation which does not exceed the threshold value stored in the database, computer 6 generates a positive evaluation of optic 2. If the recording of the reference grid and/or reference markers includes a variation in a range comprising the threshold value, computer 6 can generate an evaluation which lies between the negative and the positive evaluation, wherein advice is for instance given to use optic 2 one last time.

Figure 4:
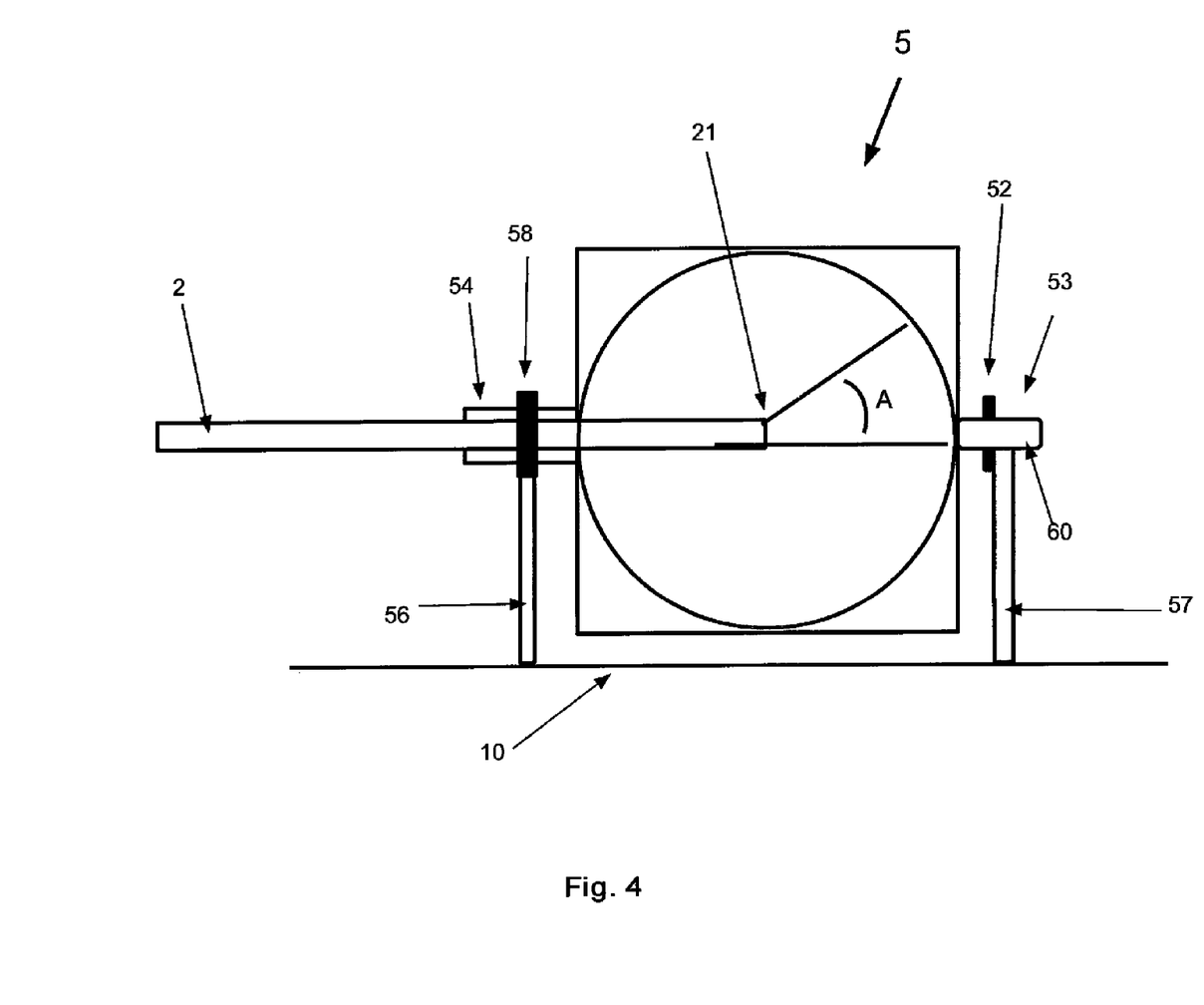
FIG. 4 shows a schematic cross-section of the second element.

FIG. 4 shows second element 5, which in this embodiment is placed on foundation 10 with a fifth and a sixth support 56, 57 of second element 5. For the purpose of securing second element 5 on foundation 10 the fifth and sixth supports 56, 57 are provided close to an outer end thereof remote from foundation 10 with a third and fourth holder 58, 52 respectively for holding protrusions 53, 54 protruding from second element 5 for fixing thereof to third and fourth holder 58, 52. The skilled person will appreciate that, for displacement of second element 5 relative to foundation 10, foundation 10 is for instance provided with guides (not shown) and second element 5 is for instance provided on a side thereof facing toward foundation 10 with guide elements (not shown) co-acting with the guides.

The protrusion 53 situated close to third holder 58 comprises a micro-camera 60, which type of camera is for instance placed in mobile telephones, which micro-camera 60 is adapted to make a recording of the tip of optic 2 situated at the first outer end 21 thereof. The recording of the tip of optic 2 records a condition of a light conductor of optic 2 close to the first outer end 21 thereof for a detection of possible breaks of glass fibres (not shown) present in the light conductor.

A recording made with micro-camera 60 can be stored in the database of computer 6 for comparison thereof to a reference image which is associated with optic 2 and stored in the database of computer 6 and which comprises information for a quantity of light coming from light source 7. If the recording of the quantity of light includes a variation which exceeds a threshold value stored in the database, computer 6 generates a negative evaluation of optic 2. If the recording of the quantity of light includes a variation which does not exceed the threshold value stored in the database, computer 6 generates a positive evaluation of optic 2. If the recording of the quantity of light includes a variation in a range comprising the threshold value, computer 6 can generate an evaluation which lies between the negative and the positive evaluation, wherein advice is for instance given to use optic 2 one last time.

Figure 5A:
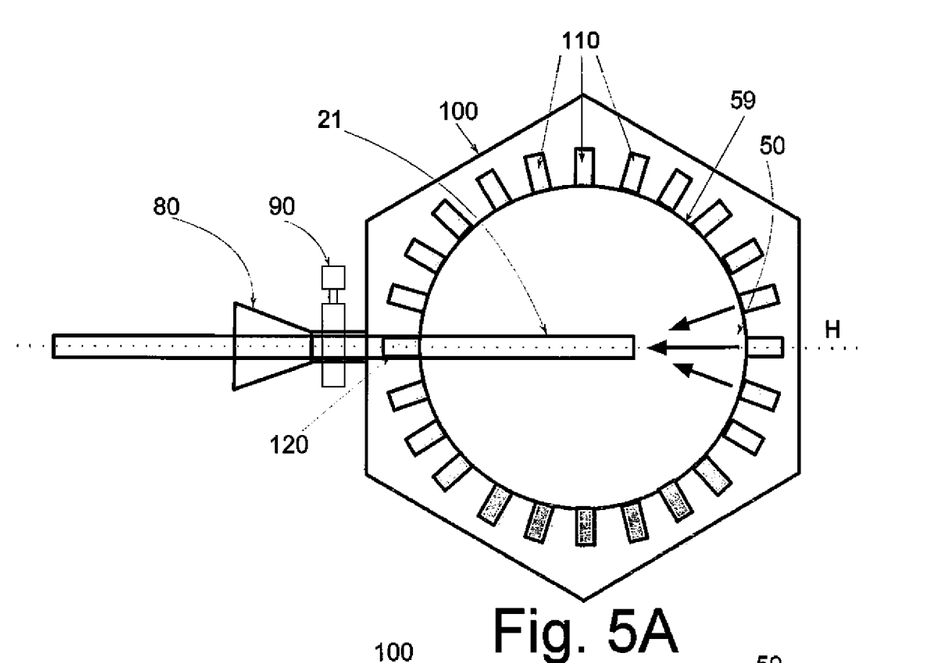
FIG. 5A shows a top view of the test image housing.

FIG. 5A shows a top view of test image housing 100. The inner side of the test image housing has a concave surface 59 on which test image 50 is arranged. The second, distal outer end 21 of the optic penetrates test image housing 100 via throughfeed 120. Test image housing 100 is preferably equipped for this purpose with a funnel-shaped part 80 with which the outer end 21 can be guided to throughfeed 120. Centering means 90 are preferably arranged between funnel-shaped part 80 and throughfeed 120 for the purpose of centering outer end 21 in tubular throughfeed 120.

Test image housing 100 is preferably provided with a second light source comprising a plurality of light elements 110.

Figure 5B:
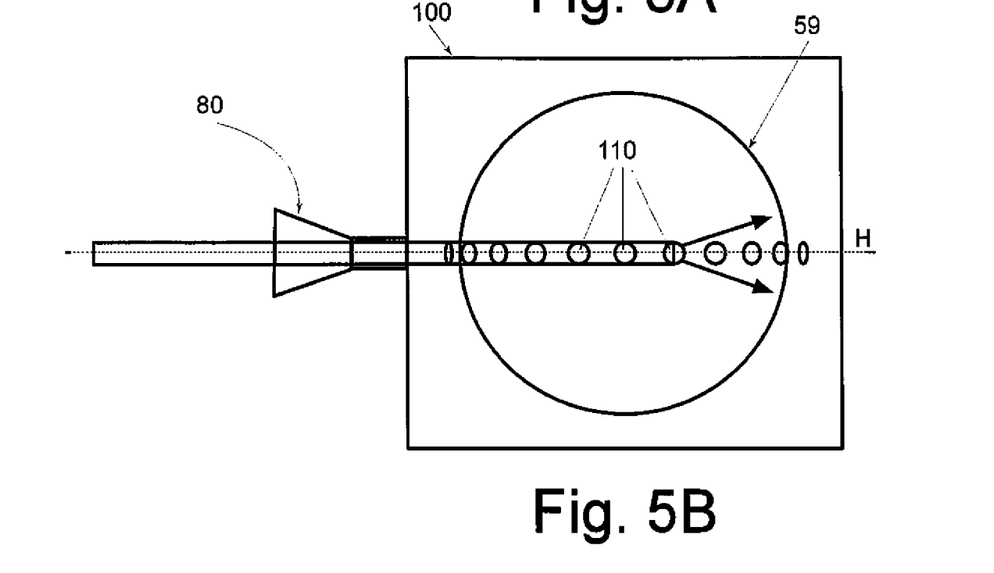
FIG. 5B shows a side view of the test image housing provided with a second light source comprising a plurality of light elements.

FIG. 5B shows a side view of test image housing 100. Light elements 110 are preferably distributed uniformly over a plane through the longitudinal axis H of the device and over part of the inner surface of test image housing 100. The light elements are preferably LEDs, which generate hardly any heat.

Figure 6A:
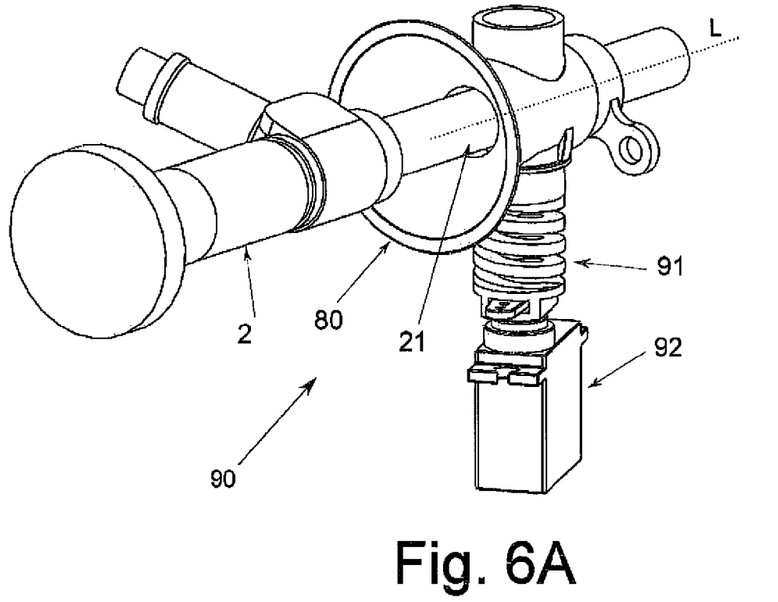
FIG. 6A shows an enlargement of the optic which is arranged in the funnel-shaped part and the centering means.

FIG. 6A shows an enlargement of optic 2 arranged in funnel-shaped part 80 and centering means 90. In the figure the centering means 90 ensure that outer end 21 of optic 2 is centred in the throughfeed. Since the longitudinal axis L of the throughfeed is the same as the central axis of funnel-shaped part 80, outer end 21 is also centred in funnel-shaped part 80. Centering means 90 can be adjusted via an adjusting screw 91, which can be operated manually as well as by means of a connected motor 92 in an automated process. Centering means 90 are preferably embodied in a soft material such that the chance of damage to optic 2 is minimized. The position of the U-shaped centering parts 93 and 94 is on longitudinal axis L of the throughfeed.

Figure 6B:
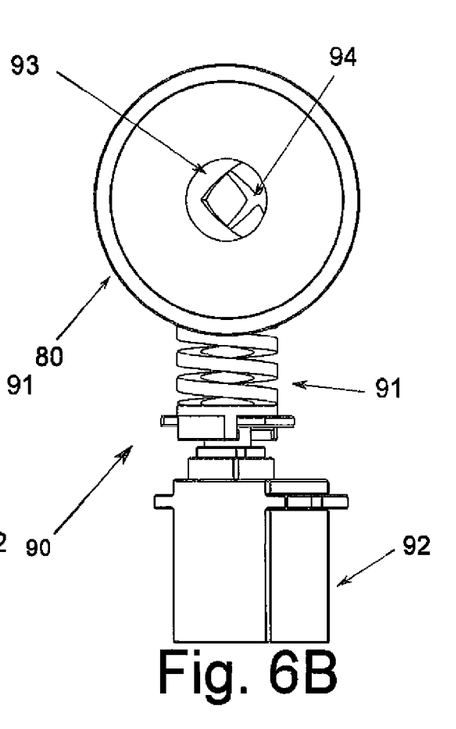
FIG. 6B shows the centering means in a first end position.

FIG. 6B shows centering means 90 in a first end position, in which centering parts 93 and 94 form a lozenge-shaped passage 95.

Figure 6C:
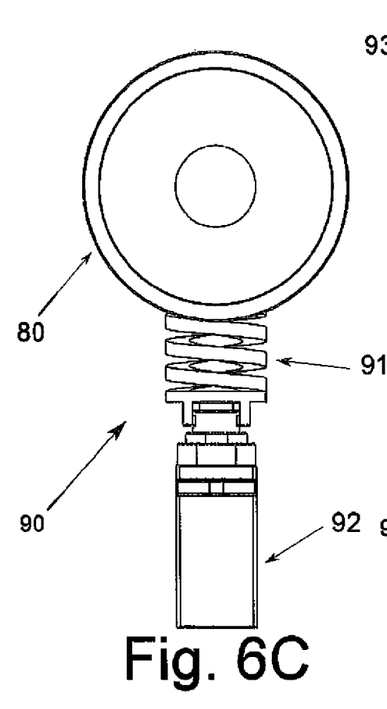
FIG. 6C shows the centering means in a second end position.

FIG. 6C shows centering means 90 in a second end position, in which centering parts 93 and 94 are wholly concealed from view.

Figure 7A:
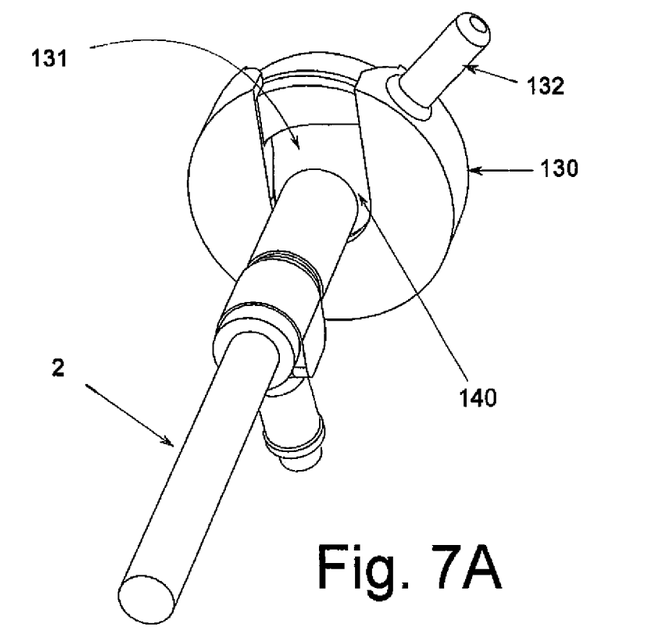
FIG. 7A shows the attaching device in which an eyepiece is attached.

FIG. 7A shows attaching device 130 in which an eyepiece 140 is attached. Eyepiece 140 is attached to the proximal outer end of optic 2. Eyepiece 140 tapers in the viewing direction thereof and is substantially round in radial direction. Eyepiece 140 is arranged in attaching device 130 via U-shaped opening 131, through which the tapering part of eyepiece 140 is guided. Eyepiece 140 is then enclosed in attaching device 130 by means of rotation of rotating rod 132 of attaching device 130.

Figure 7B:
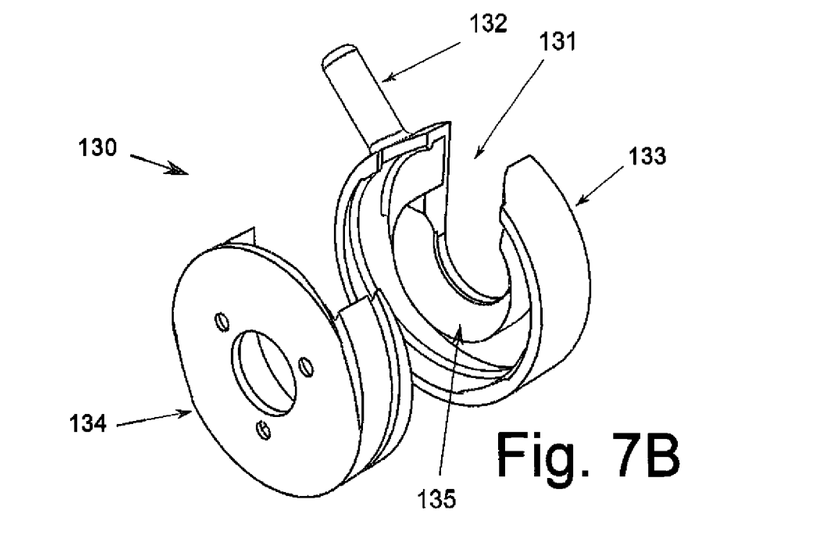
FIG. 7B shows an exploded view of the attaching device 130.

FIG. 7B shows an exploded view of attaching device 130. Attaching device 130 comprises a first housing part 133 which has a passage 131 for throughfeed of at least a part of the tapering part of the eyepiece or an extension thereof, and a second housing part 134 which intended to be clampingly received in first housing part 131. The clamping is preferably realized by means of a screw connection which can be rotated by means of rotating rod 132. Second housing part 134 is also intended to receive the proximal outer end of the eyepiece. First housing part 133 has a tapering collar 135 intended for receiving the tapering part of the eyepiece.

The invention is of course not limited to the described and shown preferred embodiment(s). The invention relates generally to any embodiment falling within the scope of protection as defined in the claims and as seen in the light of the foregoing description and accompanying drawings.

The invention claimed is:

1. A device (1) for testing a medical optic (2), such as an endoscope, a laparoscope, an arthroscope or a bronchoscope, wherein the optic (2) has a central axis extending in the longitudinal direction thereof and the optic (2) is mountable on the device (1) along the central axis, comprising:
    a test image (50),
    a test image table (10) for supporting the test image (50),
    a first light source (7) for lighting the test image (50) via the optic (2) mountable thereon,
    an attaching device (3) for mounting the optic (2),
    detection means (42, 43, 45) placed on the attaching means (3) for detecting the lighted test image (50),
    first guide means (39) and second guide means (19) co-acting with the first guide means (39) and extending in longitudinal direction thereof for the purpose of positioning the test image table (10) along a substantially straight line relative to the attaching device (3), and
    a signal processing device (6) for receiving, storing and comparing detection values of the lighted test image (50) detected by the detection means (42, 43, 45) to threshold values therefor specific to the optic (2) and prestored in a database,
wherein the first (39) and/or the second guide means (19) are situated parallel to and at a distance from the central axis of the optic (2), the attaching device (3) for mounting the optic (2) is adjustable relative to the test image (50) along the longitudinal direction of the optic (2), the first guide means (39) are arranged on the attaching device (3) and the second guide means (19) are arranged on the test image table (10) for relative displacement of the attaching device (3) relative to the test image (50), a servomotor (11) is adapted to displace the attaching device (3) relative to the test image (50) in the longitudinal direction of the optic (2), characterized in that the optic (2) is provided with identification elements (20) and wherein the device (1) is provided with read elements (60) for reading the identification elements (20).

2. A device (1) as claimed in claim 1, wherein the identification elements (20) comprise a barcode etched into the optic (2) and wherein the read elements (60) comprise a barcode scanner.

3. A device (1) as claimed in claim 1, wherein the servomotor (11) is adapted to drive a displacement of the attaching device (3) relative to the test image (50) subject to identification elements (20) detected by the read elements (60).

4. A device (1) as claimed in claim 1, wherein the test image (50) is mounted on a concavely formed surface of a spherical surface (59).

5. A device (1) as claimed in claim 4, wherein the test image (50) is provided with a pattern which comprises information distributed concentrically over the concavely formed surface relative to the centre of the spherical surface (59).

6. A device (1) as claimed in claim 1, wherein the test image (50) comprises a grid and/or a pattern of markers.

7. A device (1) as claimed in claim 4, wherein the device (1) comprises a test image housing (100) with a substantially closed inner space provided with an at least partly spherical surface, and the test image (50) is arranged on the spherical surface and the test image housing (100) comprises a throughfeed (120) for throughfeed of a distal outer end (21) of the optic (2).

8. A device (1) as claimed in claim 7, wherein the throughfeed (120) is provided with centering means (90) for centering the distal outer end (21) of the optic (2) in the throughfeed (120), and wherein the centering means (90) are adapted to centre distal outer ends (21) of different diameter.

9. A device (1) as claimed in claim 8, wherein the centering means (90) comprise two substantially V-shaped, co-acting centering parts (93, 94) at a certain mutual distance on the longitudinal axis (H) of the throughfeed (120) which, as seen in the line of the throughfeed (120), form a substantially lozenge-shaped passage, and the centering parts (93, 94) are movable adjustably between a first and second end position, wherein in the first end position the centering parts (93, 94) lie substantially at a right angle to the longitudinal axis (H) of the throughfeed (120) and in the second end position the centering parts (93, 94) each lie at an acute or obtuse angle relative to the longitudinal axis (H) of the throughfeed (120) such that the size of the lozenge-shaped passage is adjustable.

10. A device (1) as claimed in claim 7, wherein the test image housing (100) comprises a funnel-shaped part (80) adjacently of the throughfeed (120) for guiding the distal outer end (21) of the optic (2) to the throughfeed (120).

11. A device (1) as claimed in claim 7, wherein the test image housing (100) is provided with a second light source (110).

12. A device (1) as claimed in claim 11, wherein the second light source (110) comprises a plurality of light elements such as LEDs distributed over an inner surface of the test image housing (100).

13. A device (1) as claimed in claim 1, wherein the detection means (42, 43, 45) comprise a colour analyser for determining a colour of the light which comes from the first and/or second light source (110) and which the test image (50) projects onto the colour analyser, and the signal processing device (6) is adapted to store and compare received colour detections to the threshold values therefor specific to the optic (2) and prestored in a database.

14. A device (1) as claimed in claim 1, wherein the detection means (42, 43, 45) comprise a moisture measuring device for detecting moisture at least close to lens transitions in the optic (2), and wherein the signal processing device (6) is adapted to store and compare received moisture detections to the threshold values therefor specific to the optic and pre-stored in a database.

15. A device (1) as claimed in claim 14, wherein the moisture measuring means comprises a microwave sensor for generating a microwave directed through the optic (2) and for receiving a signal influenced by a lens transition and directed toward the microwave sensor.

16. A device (1) as claimed in claim 1, wherein the camera is provided with adjusting means for focussing a lens of the camera on the different lens transitions, wherein the adjusting means can be controlled by the signal processing device (6) to focus on the lens transitions of the optic (2) subject to setting values specific to the optic (2) and stored in the database.

17. A device (1) as claimed in claim 1, wherein the test image (50) comprises a narrow continuous opening at the position of an extended central axis in the longitudinal direction of the optic (2) which can be mounted in the attaching device (3), and wherein a micro-camera (60) is placed close to the test image (50) on a side thereof remote from the optic (2) which can be mounted in the attaching device (3).

18. A device (1) as claimed in claim 1, wherein the detection means (42, 43, 45) comprise a light intensity meter for determining the intensity of the light exiting the optic (2) close to the proximal outer end, and the signal processing device (6) is adapted to store and compare the measured light intensity to threshold values therefor specific to the optic (2) and are pre-stored in a database.

19. A device (1) as claimed in claim 1, wherein the attaching device (3) comprises two co-acting housing parts (133, 134), wherein
    the first housing part (133) has a passage for throughfeed (120) of at least a part of a tapering part of an eyepiece (140) of the optic (2) or an extension thereof,
    the first housing part (133) has a tapering collar (135) intended for the purpose of receiving the tapering part of the eyepiece,
    the second housing part (134) is intended for the purpose of receiving the free outer end of the eyepiece,
    the second housing part (134) is intended to be received in closing manner in the first housing part (133).

* * * * *